United States Patent [19]

Suhr et al.

[11] 4,449,411

[45] May 22, 1984

[54] MAGNETIC AND ULTRASONIC OBJECTS TESTING APPARATUS

[75] Inventors: Peter J. Suhr, Westbury; Robert A. Brooks, Rye, both of N.Y.; Terrance R. Banach, Danbury, Conn.

[73] Assignee: Magnetic Analysis Corporation, Mt. Vernon, N.Y.

[21] Appl. No.: 370,830

[22] Filed: Apr. 22, 1982

[51] Int. Cl.³ .................... G01N 29/04; G01R 33/12
[52] U.S. Cl. ................................ 73/643; 324/226; 324/227
[58] Field of Search ................ 73/643; 324/226, 227

[56] References Cited

U.S. PATENT DOCUMENTS

| | | | |
|---|---|---|---|
| 3,237,446 | 3/1966 | Wood | 324/227 |
| 3,460,063 | 8/1969 | Houck et al. | 340/15 |
| 3,583,213 | 6/1971 | Houck et al. | 73/67.5 |
| 3,588,682 | 6/1971 | Forster | 324/37 |
| 3,609,531 | 9/1971 | Forster | 324/37 |
| 3,854,085 | 12/1974 | Mansson et al. | 324/37 |
| 4,096,437 | 6/1978 | Kitzinger et al. | 324/227 |
| 4,309,905 | 1/1982 | Maizenberg et al. | 73/643 |

FOREIGN PATENT DOCUMENTS

| | | | |
|---|---|---|---|
| 646178 | 8/1962 | Canada | 324/226 |
| 24707 | 3/1981 | European Pat. Off. | |
| 2006433 | 5/1979 | United Kingdom | |
| 7584799 | 2/1981 | United Kingdom | |
| 2064772 | 6/1981 | United Kingdom | |

OTHER PUBLICATIONS

"EDW-T Electrodynamic Transducer", of NUKEM GmbH.

Primary Examiner—Howard A. Birmiel
Attorney, Agent, or Firm—James J. Daley

[57] ABSTRACT

Nondestructive object testing is carried out in a magnetic aspect as by leakage-flux detection and in an ultrasonic aspect by electromagnetic acoustic wave generation and detection, portions of magnetic flux being derived from a common source for the respective magnetic and ultrasonic testing.

15 Claims, 7 Drawing Figures

MAGNETIC AND ULTRASONIC OBJECTS TESTING APPARATUS

FIELD OF INVENTION

This invention relates generally to nondestructive object testing and pertains more particularly to apparatus and methods for combined magnetic and ultrasonic object examination.

BACKGROUND OF THE INVENTION

Three widely practiced techniques are presently in extensive commercial use in nondestructive object testing, namely, leakage flux detection, eddy current measurement and acoustic wave examination. The first two named techniques have in common transferring to the test object a magnetic flux either for eddy current generation in the surface thereof or for so saturating the object as to force flux exterior to the object where flaws exist. Present commercial versions of the acoustic wave technique are based upon the use of a magnetic field cooperatively with an acoustic wave generated by a piezoelectric device and applied to the object by a fluid medium couplant. The leakage flux and eddy current techniques may be categorized as magnetic and the magnetic/acoustic technique may be categorized as ultrasonic.

In the ultrasonic area, a development of the recent decades offers benefit in its elimination of the couplant medium. The couplant has been a bothersome element and occasions have arisen where, despite that the test environment or test object has called for ultrasonic practice as uniquely applicable, the testing has either been done by other technique or has been foregone since use of the couplant is not permitted. The referenced recent development, as set forth, for example, in U.S. Pat. Nos. 3,460,063 and 3,583,213, is the observation of the phenomenon of electromagnetically inducing an acoustic wave in an object under steady-state magnetic field influence. While the theoretical aspects of this technique are extensively treated in published literature, the development has not shown industry-wide impact to this time.

One characteristic of known nondestructive testing apparatus and methods is that the various systems are made commercially available independently of one another. Thus, present commercial magnetic category products are for either leakage flux testing or eddy current measurement to detect object characteristics and do not incorporate ultrasonic apparatus of the piezoelectric type or of EMAT (electromagnetic acoustic transducer) type, and vice versa. The user industry has not heretofore been provided with apparatus and methods which look to the testing of objects commonly by both magnetic and ultrasonic techniques, particularly the more conveniently usable of the known ultrasonic techniques.

SUMMARY OF THE INVENTION

The present invention has as its object the provision of improved apparatus and methods for nondestructive testing of objects.

It is a more particular object of the invention to provide apparatus and methods for combined magnetic and ultrasonic object testing.

In attaining these and other objects, the invention provides for the derivation from a common source of magnetic flux of first and second magnetic flux portions, respectively for use in magnetic and ultrasonic object examination. In particularly preferred practice, the invention calls for definition of a path therethrough for movement of a test object, provides a common source of magnetic flux and uses portions of such flux for establishing a first magnetic field for saturation of the object to enable leakage flux measurements and for establishing a second magnetic field for EMAT testing of the object.

Apparatus in accordance with the invention includes magnetic flux generating means in flux receiving communication with both of first and second pole pieces for defining such first and second magnetic flux portions, a leakage flux detector coactive with the first flux portion and an EMAT transducer supported with its transduction directional sense being aligned with the directivity of the second flux portion. In one embodiment, the invention provides apparatus wherein the first and second pole pieces are spatially coincident, i.e., the EMAT probe pole piece is disposed in the other pole piece. In a preferred embodiment, the EMAT pole piece is longitudinally displaced along the path of object movement from the other pole piece.

The foregoing and other features of the invention will be further understood from the following detailed description of the preferred embodiment and by reference to the drawings wherein like reference numerals identify like parts throughout.

DESCRIPTION OF THE PREFERRED EMBODIMENTS

As alluded to above, the art is familiar with eddy current and leakage flux practices and apparatus, varieties of which are commercially available and described in published literature and patents. With respect to leakage flux apparatus, incorporating reference is now made to U.S. Pat. No. 3,854,085, FIGS. 3 and 4 of which correspond in major part to FIGS. 1 and 2 hereof.

Figures 1, 2:
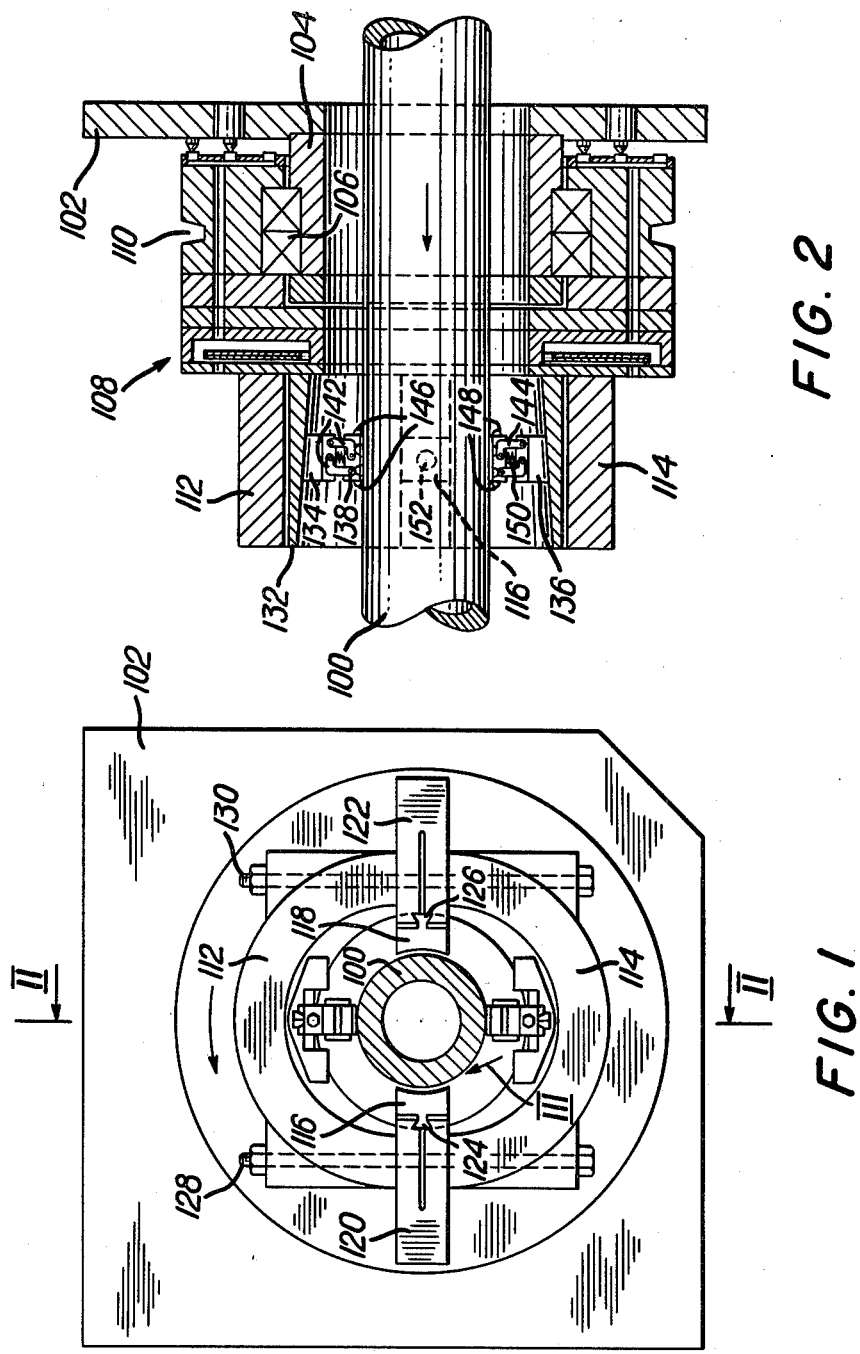
FIG. 1 is front elevation of a testing head in accordance with the invention.
FIG. 2 is a sectional view of the FIG. 1 testing head as would be seen from plane II—II of FIG. 1.

Turning to FIGS. 1 and 2, they illustrate a rotating head arrangement which is usually more convenient than a fixed arrangement when tubing and bar stock is to be tested, since the object 100 requires only longitudinal movement which can be produced by conventional conveyers, such as rollers. A fixed back plate 102 has a hub 104 affixed thereto, and the hub carries a set of bearings 106 on which the head generally designated 108 rotates. The head may be driven by a motor and belt (not shown), the belt engaging in groove 110. Various parts of the fixed and rotating structures are held together by bolts, etc., but these are omitted for the most part to avoid complicating the drawings.

A permanent magnet is mounted on the rotating head and is here shown as a pair of half-cylinders 112 and 114, between which pole pieces 116 and 118 are held by clamping members 120 and 122 forming part of the magnet structure. Dove-tail and groove connections 124 and 126 between the pole pieces and clamping members, with the grooves inclined to the axis of rotation allow the pole pieces to be adjusted with respect to the axis to accommodate different diameter pieces. The clamping members are slotted so that the pole pieces can be held in the desired positions by tightening the nuts on bolts 128 and 130. The bolts pass through ears of the magnet and through the clamping members.

A tapered member 132 is also attached to the rotating head 108 for mounting the probe carries 134 and 136 in inclined dove-tail and groove manner similarly to the pole pieces to allow adjustment for different diameter pieces. Suitable locking means is provided such as a split dove-tail and an expansion screw. In this embodiment each probe carrier supports a probe cartridge 138 and 140 by means of lever arms 142 and 144 and the cartridges have projections 146 and 148 thereon serving as lifting ramps and riding shoes. Thus, if the space between the probe cartridges is less than the diameter of object 100, as the piece enters it will strike the ramps and move the cartridges outward to avoid damage. Thereafter the cartridges will be maintained in contact with object 100 by compressions springs 150 and the probes will scan the material with a fixed air gap. As respects probe configuration and circuit connections, same are set forth in U.S. Pat. No. 3,854,085, to which reference is invited.

Figure 3:
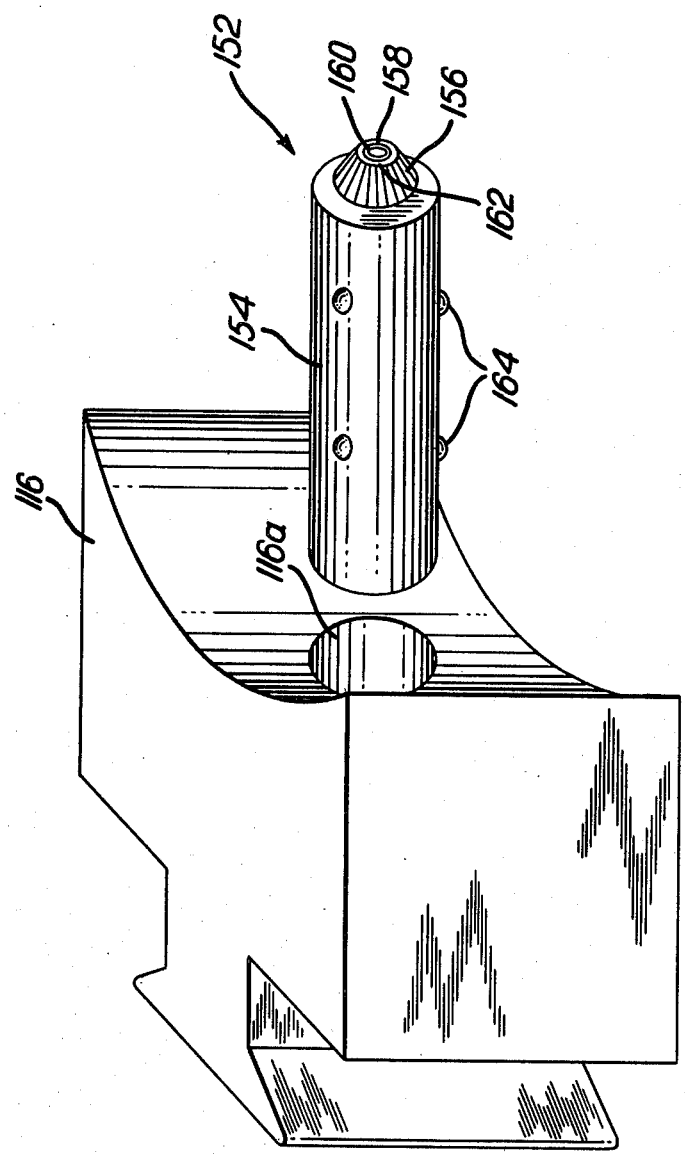
FIG. 3 is a perspective view of the leftward leakage flux pole piece of the FIG. 1 testing head as would be seen in the direction of arrow III in FIG. 2, the view also showing in exploded manner the EMAT unit resident in the pole piece.

Such known described apparatus is modified in accordance with the invention by introducing EMAT device 152. As is seen in FIG. 3, a central opening 116a is provided in magnet 116 for seating of device 152, which itself comprises a pole piece 154, an end member 156 and EMAT transmitting and receiving coils 158 and 160, secured in casing 162. Spring loaded ball bearings 164 are seated in pole piece 154 to define an air gap between the pole piece and magnet 116 and to facilitate insertion of EMAT device 152 therein.

Referring to the alternate embodiment of apparatus in accordance with the invention, shown in FIGS. 4-7, electromagnetic acoustic wave object examination apparatus 10 includes steady-state or quasi-static magnetic field generating means 12 having half cylindrical elements 14, 15, 16 and 17. Magnetic flux coupler 18 spans elements 14 and 16 vertically and is suitably mechanically secured thereto in fixed disposition. Pole piece 24 is releasably securable in coupler 18, threadable members 25 and 27 being insertable therein for securement of pole piece 24 on apparatus assembly and for release thereof to adjust the pole piece for different sized test objects.

Pole piece 24 has a reduced rightward portion 24a which has vertical sides 24a-1 and 24a-3 and tapered forward wall 24a-2. EMAT probe 34 preferably is comprised of a pair of concentrically arranged coils 34a and 34b, supported in a flat synthetic plastic casing 34c. A commercially available version of usable transducer is incorporated in an EMAT probe available from NUKEM GmbH of Germany as Electrodynamic Transducer EDW-T. Casing 34c is circumscribed by frusto-conical metal end member 36, serrated as indicated by slits 36a at fifteen degree circumferential intervals.

Figure 4:
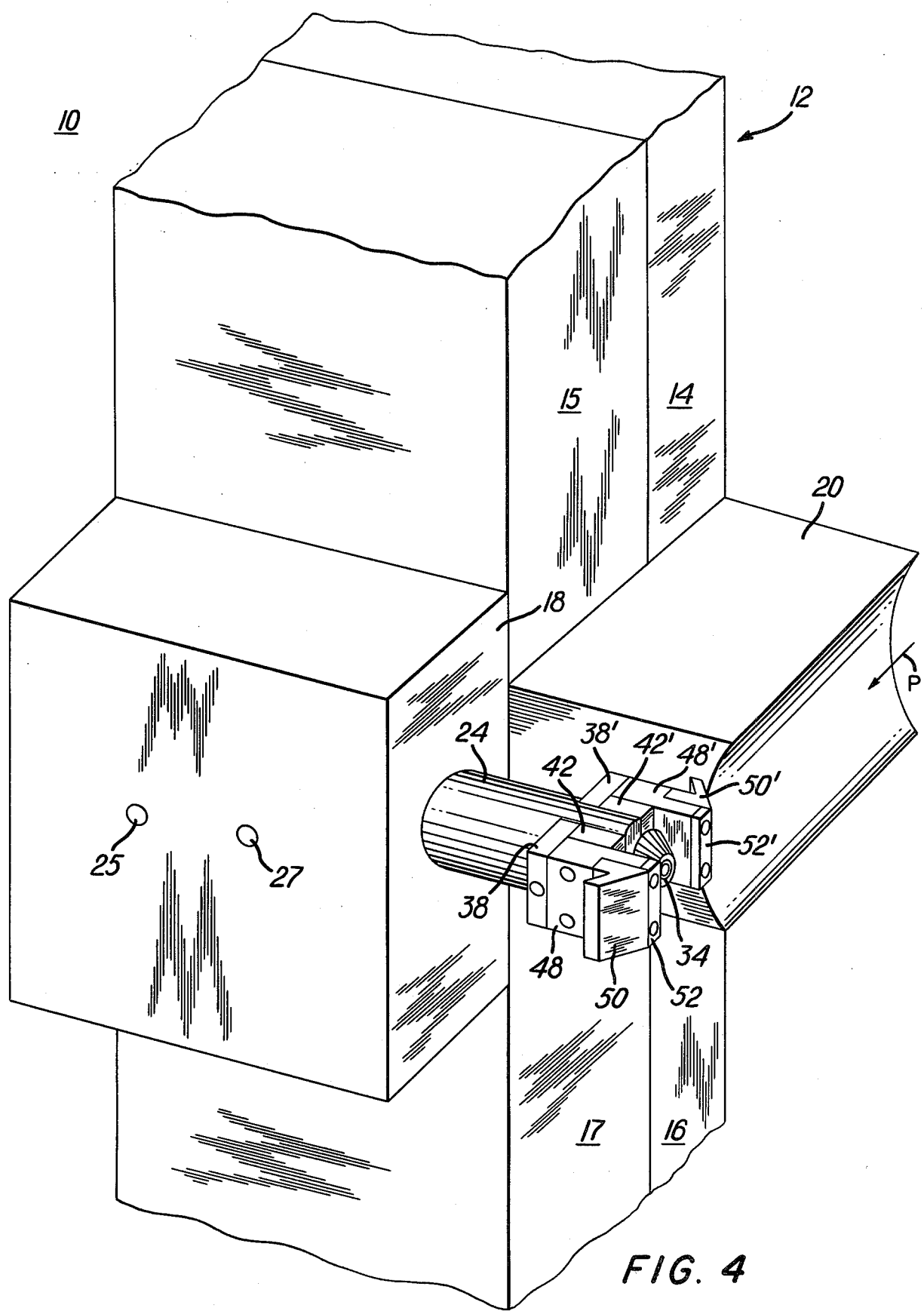
FIG. 4 is a partial perspective view of another embodiment of apparatus in accordance with the invention with an EMAT probe and pole piece shown in operative position.
Figure 6:
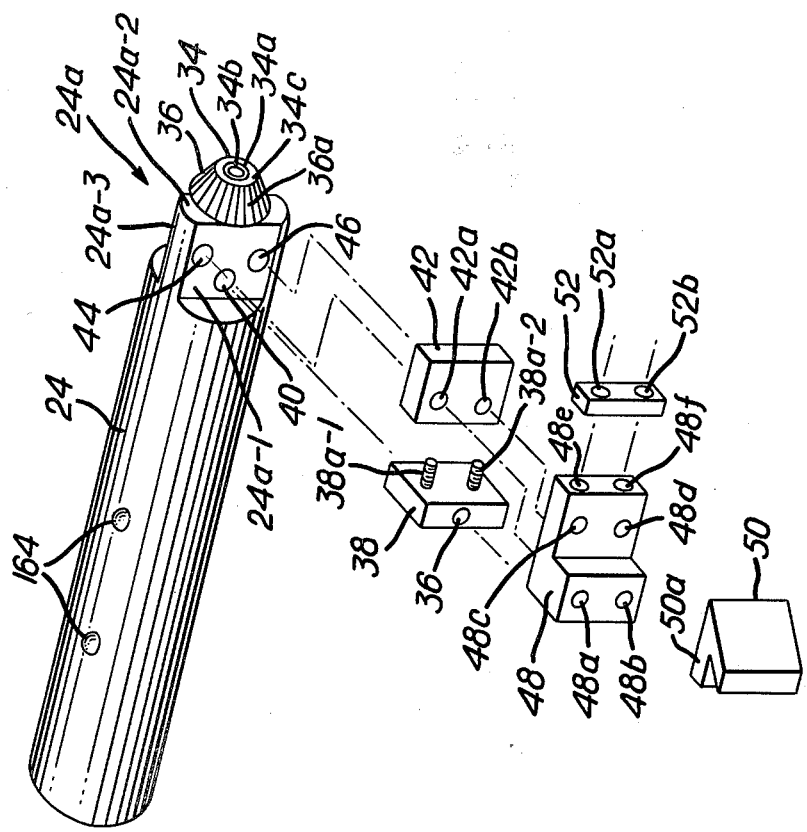
FIG. 6 is a partial perspective view of the FIG. 4 EMAT probe and pole piece with the EMAT guard and gap control means being shown in exploded fashion to indicate assembly and structural detail.
Figure 5:
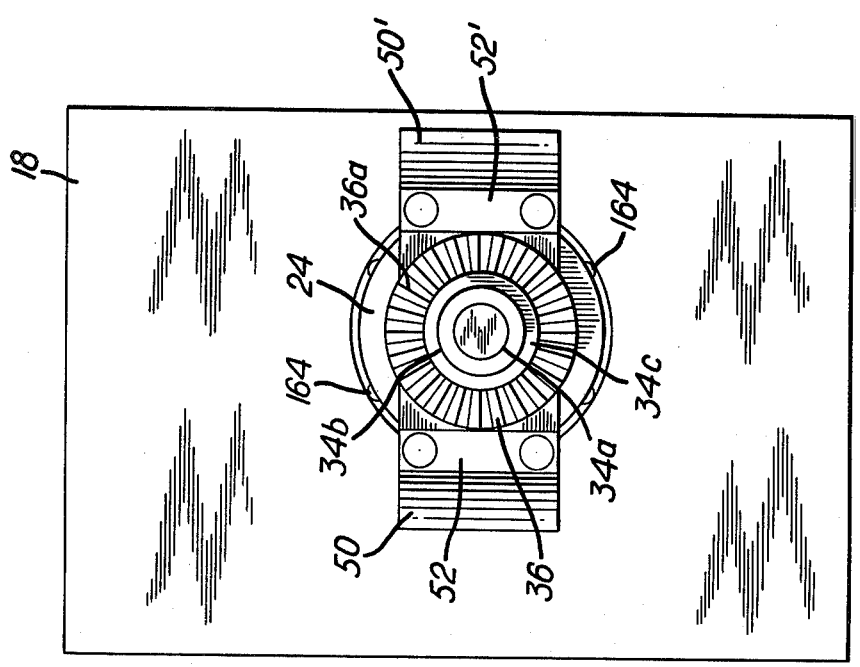
FIG. 5 is side elevational view as would be seen rightwardly of FIG. 1.

Turning now to the exploded component showings in FIG. 6, and the assembled showings thereof in FIGS. 4 and 5, adjusting block 38 supports set screws 38a-1 and 38a-2 for trimming the position of guard 48 and includes throughbore 38b registrable with pole piece threaded bore 40. Filler piece 42 nests behind end member 36 and abuts block 38 and has throughbores 42a and 42b registrable with pole piece threaded bores 44 and 46.

Guard support 48 has throughbores 48a and 48b registrable with bores 42a and 42b of filler piece 42 and includes a recessed land 48c for seating of sideguard 50. Sideguard 50 has throughbores (not shown) extending through arm 50a and registrable with threaded bores 48c and 48d of support 48. End guard 52, preferably a carbide, has throughbores 52a and 52b registrable with threaded bores 48e and 48f of support 48. Screws provide assembly of the components as indicated in FIGS. 4 and 5, which also show the counterpart opposite side components 38', 42', 48', 50' and 52'.

As assembled and in operative position, carbides 52 and 52' engage a test object 54 (FIG. 7), spacing EMAT probe 34 therefrom by distance D, i.e., the transduction air gap, which is desirably about one and one-half millimeters. Further, together with sideguards 50 and 50', the carbides protect the EMAT probe from damage from the test object during its movement into operative position.

Figure 7:
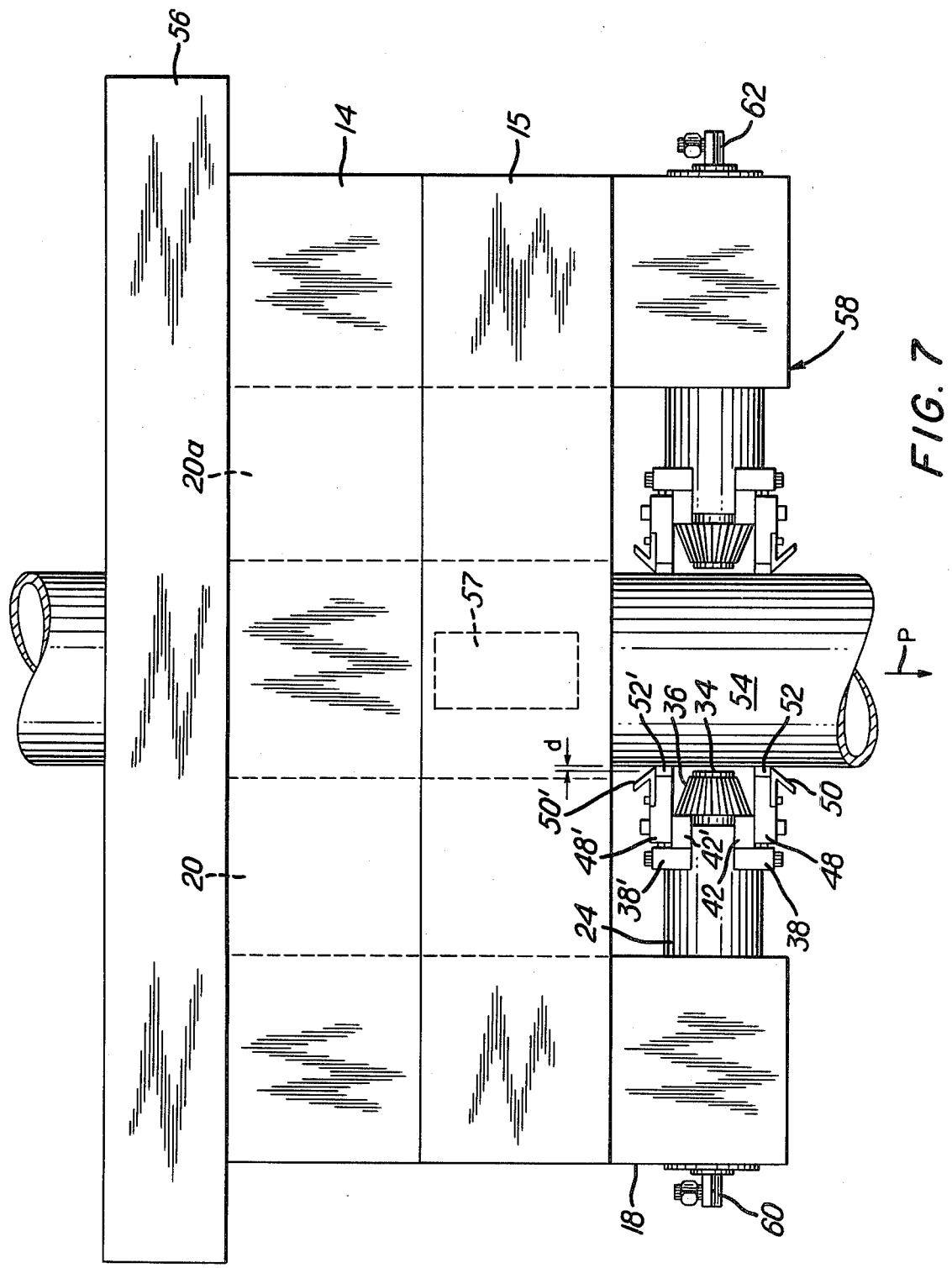
FIG. 7 is a complete top plan view of the FIG. 4 apparatus, shown with support for rotative movement thereof about a test object in the form of a thin-walled metal pipe.

In the complete top plan view of FIG. 7, upper magnets 14 and 15 and the unshown lower magnets 16 and 17 are secured to head plate 56 which is preferably supported for rotation about path P by a rotating head arrangement, such as discussed above in connection with FIGS. 1 and 2. Also seen in FIG. 7 is the other leakage flux pole piece 20a leakage flux detector 57 and a second EMAT apparatus 58, identical to the EMAT apparatus of FIG. 4. Electrical connections are made through connector pairs 60 and 62 for furnishing radio frequency excitation to transmitting coil 34a (FIG. 1) of EMAT probe 34 and for processing the output signals of coil 34b. This wound coil typically has fifteen turns and receiving coil 34b typically has one to three hundred turns. Excitation is typically pulsed three hundred volts at radio frequency, these parameters being selected on balance in conjunction with magnetic field strength and magnitude of flux provided to the object at the transduction surface and the characteristics of the object. These matters, as well as underlying theory and received signal processing practices are set forth in part in U.S. Pat. Nos. 3,583,213 and 3,460,063 referred to above and otherwise in published literature, to which reference may be made.

Various changes may evidently be made to the foregoing particularized embodiment and practice without departing from the invention. Accordingly, the depicted preferred embodiment is intended in an illustrative and not in a limiting sense. The true spirit and scope of the invention are set forth in the following claims.

We claim:

1. Apparatus for nondestructive object testing comprising:

(a) a source generating magnetic flux;

(b) first and second pole piece means for receiving respective portions of such generated flux and for transferring received flux therefrom;

(c) detector means responsive to flux transferred to said object by said first pole piece means for determining characteristics of said object; and (d) electromagnetic acoustic transducer means coactive with flux transferred to said object by said second pole piece means for determining characteristics of said object.

2. The apparatus claimed in claim 1 wherein said detector means is disposed remotely from said first pole piece means and proximate said object and wherein said transducer means is disposed proximate said second pole piece means and proximate said object.

3. The apparatus claimed in claim 1 wherein said apparatus defines a path for insertion of said object, said first and second pole piece means being disposed with respect to said insertion path along a common axis intersecting said insertion path.

4. The apparatus claimed in claim 1 wherein said apparatus defines a path for insertion of said object, said first and second pole piece means being disposed at respective different locations along said insertion path.

5. The apparatus claimed in claim 1 wherein said apparatus defines a path for insertion of said object, said apparatus further including drive means for jointly rotating said means (a) through (d) about said insertion path.

6. Apparatus for nondestructive object testing comprising:

(a) means for generating magnetic flux;

(b) first and second pole piece means for receiving respective portions of said generated flux, each such pole piece means including plural pole pieces spaced from one another about an object insertion path in said apparatus;

(c) detector means proximate said insertion path at a location between such pole pieces of said first pole piece means for determining characteristics of said object; and (d) electromagnetic acoustic transducer means so disposed with respect to said pole pieces of said second pole piece means as to have its directional transduction sense aligned with the flux issuance direction of at least one of said pole pieces of said second pole piece means.

7. The apparatus claimed in claim 6 wherein said transducer means comprises a single EMAT transducer disposed adjacent said one pole piece of said second pole piece means.

8. The apparatus claimed in claim 7 wherein said detector means is disposed remotely from each of said pole pieces of said first pole piece means.

9. The apparatus claimed in claim 8 where corresponding pole pieces of said first and second pole piece means are disposed with respect to said object insertion path along a common axis intersecting said insertion path.

10. The apparatus claimed in claim 8 wherein corresponding pole pieces of said first and second pole piece means are disposed at respective different locations along said insertion path.

11. The apparatus claimed in claim 6 further including drive means for jointly rotating said means (a) through (d) about said insertion path.

12. Method for nondestructive testing of an object comprising the steps of:

(a) defining a path for movement of said object for testing thereof;

(b) providing a common source of magnetic flux;

(c) establishing with a first portion of said magnetic flux a first magnetic field sufficient to magnetically saturate said object on movement thereof in said path;

(d) establishing with a second portion of said magnetic flux a second magnetic field in said path;

(e) detecting leakage flux from said object; and (f) generating through use of said second magnetic field an electromagnetic acoustic wave in said object and detecting said wave as reflected from said object.

13. The method claimed in claim 12 wherein said path is selected to be elongate and wherein said first and second magnetic fields are generated along a common axis intersecting said path.

14. The method claimed in claim 12 wherein said path is selected to be elongate and wherein said first and second magnetic fields are generated at a respective first and second different longitudinal locations along said path.

15. The method claimed in claim 12 wherein relative rotational movement is effected during such testing as between (a) said object and (b) said first and second magnetic fields.

* * * * *